US009474500B2

(12) United States Patent
Poon et al.

(10) Patent No.: US 9,474,500 B2
(45) Date of Patent: Oct. 25, 2016

(54) METHOD AND SYSTEM FOR TRANSFER OF CARDIAC MEDICAL IMAGE DATA FILES

(75) Inventors: Michael Poon, Harrington Park, NJ (US); Satya P. Sharma, Setauket, NY (US); Arie Kaufman, Plainview, NY (US); Rong Zhao, Mount Sinai, NY (US); Jacob Sharony, Dix Hills, NY (US)

(73) Assignee: The Research Foundation of State University of New York, Albany, NY (US)

( * ) Notice: Subject to any disclaimer, the term of this patent is extended or adjusted under 35 U.S.C. 154(b) by 759 days.

(21) Appl. No.: 13/146,465

(22) PCT Filed: Feb. 5, 2010

(86) PCT No.: PCT/US2010/023351
§ 371 (c)(1),
(2), (4) Date: Dec. 22, 2011

(87) PCT Pub. No.: WO2010/091273
PCT Pub. Date: Aug. 12, 2010

(65) Prior Publication Data
US 2012/0087560 A1    Apr. 12, 2012

Related U.S. Application Data

(60) Provisional application No. 61/150,173, filed on Feb. 5, 2009.

(51) Int. Cl.
G06K 9/00    (2006.01)
G06K 9/36    (2006.01)
A61B 6/00    (2006.01)
A61B 6/03    (2006.01)
G06F 19/00    (2011.01)

(52) U.S. Cl.
CPC .............. *A61B 6/563* (2013.01); *A61B 6/032* (2013.01); *G06F 19/321* (2013.01); *A61B 6/503* (2013.01)

(58) Field of Classification Search
None
See application file for complete search history.

(56) References Cited

U.S. PATENT DOCUMENTS 6,157,696 A * 12/2000 Saito et al. ..................... 378/19
6,243,437 B1 * 6/2001 Hu et al. ........................ 378/8
6,498,571 B2 * 12/2002 Molloy ........................ 341/65
6,665,370 B2 * 12/2003 Bruder et al. ................ 378/15

(Continued)

FOREIGN PATENT DOCUMENTS

JP    01142872 A *    6/1989    ............. G06F 15/62

OTHER PUBLICATIONS

"Lossless Compression of 4D Medical Images Using H.264/AVC," V. Sanchez, et al, ICASSP 2006, pp. II-1116-1119, 2006.*

(Continued)

*Primary Examiner* — Wenpeng Chen
(74) *Attorney, Agent, or Firm* — McCarter & English, LLP

(57) ABSTRACT

A system and method is provided which allows for the transfer of an image data file such as a medical image data file. Device scan slices of an object are acquired per time point. A portion of the device scan slices of the object, e.g., live body organ, per time point which illustrate a change in the object from a previous time point is selected. At least one optical temporal image in spiral fashion per time interval is formed from the selected portion. The at least one optical temporal image is transmittable as an image data file to a location.

27 Claims, 4 Drawing Sheets

(56) References Cited

U.S. PATENT DOCUMENTS

| | | | |
|---|---|---|---|
| 6,937,690 B2* | 8/2005 | Bruder et al. | 378/15 |
| 7,346,108 B2* | 3/2008 | Maeda | 375/240.16 |
| 7,376,279 B2* | 5/2008 | Dekel et al. | 382/240 |
| 7,602,950 B2* | 10/2009 | Goldstein et al. | 382/128 |
| 7,929,793 B2* | 4/2011 | Gering et al. | 382/239 |
| 8,041,129 B2 | 10/2011 | Ernvik et al. | |
| 8,369,590 B2* | 2/2013 | Wang et al. | 382/128 |
| 2002/0152395 A1* | 10/2002 | Zhang et al. | 713/200 |
| 2003/0016851 A1* | 1/2003 | Kaufman et al. | 382/131 |
| 2004/0022447 A1* | 2/2004 | Mukhopadhyay et al. | 382/243 |
| 2004/0230613 A1* | 11/2004 | Goldstein et al. | 707/104.1 |
| 2005/0111746 A1* | 5/2005 | Kumar et al. | 382/248 |
| 2005/0207538 A1* | 9/2005 | Mollus et al. | 378/132 |
| 2007/0014480 A1 | 1/2007 | Sirohey et al. | |
| 2007/0189708 A1 | 8/2007 | Lerman et al. | |
| 2007/0197907 A1* | 8/2007 | Bruder et al. | 600/425 |
| 2007/0248271 A1* | 10/2007 | Sakai et al. | 382/236 |
| 2007/0269117 A1* | 11/2007 | Ernvik et al. | 382/232 |
| 2008/0069458 A1* | 3/2008 | Vega-Higuera et al. | 382/232 |
| 2008/0137922 A1* | 6/2008 | Catallo et al. | 382/128 |
| 2008/0187200 A1* | 8/2008 | Degani et al. | 382/131 |
| 2008/0219567 A1* | 9/2008 | Claus et al. | 382/131 |
| 2008/0231910 A1* | 9/2008 | Gering et al. | 358/448 |
| 2008/0232699 A1* | 9/2008 | Gering et al. | 382/232 |
| 2008/0240536 A1* | 10/2008 | Soubelet et al. | 382/132 |
| 2008/0309751 A1* | 12/2008 | Lam et al. | 348/14.08 |
| 2009/0099862 A1* | 4/2009 | Fireman et al. | 705/2 |
| 2009/0105579 A1 | 4/2009 | Garibaldi | |
| 2009/0123050 A1* | 5/2009 | Ionasec et al. | 382/131 |
| 2009/0141593 A1 | 6/2009 | Taha | |
| 2009/0141935 A1 | 6/2009 | Grass et al. | |
| 2009/0161933 A1* | 6/2009 | Chen | 382/131 |
| 2009/0232379 A1 | 9/2009 | Kohler et al. | |
| 2009/0257628 A1 | 10/2009 | Ranga et al. | |
| 2009/0279754 A1* | 11/2009 | Gindele et al. | 382/128 |
| 2009/0279756 A1* | 11/2009 | Gindele et al. | 382/128 |
| 2009/0310847 A1 | 12/2009 | Matsuzaki et al. | |
| 2010/0017182 A1 | 1/2010 | Voros et al. | |
| 2010/0067760 A1 | 3/2010 | Zhang et al. | |
| 2010/0076296 A1 | 3/2010 | Mittal et al. | |
| 2010/0086483 A1 | 4/2010 | Belardinelli et al. | |
| 2010/0104160 A1 | 4/2010 | Lavi et al. | |
| 2010/0119131 A1 | 5/2010 | Gebow | |
| 2010/0128963 A1 | 5/2010 | Waku et al. | |
| 2010/0142774 A1* | 6/2010 | Ben-Haim et al. | 382/128 |
| 2010/0246957 A1 | 9/2010 | Visser | |
| 2010/0268060 A1 | 10/2010 | Masumoto | |
| 2010/0275145 A1 | 10/2010 | Nijlunsing et al. | |
| 2010/0278405 A1 | 11/2010 | Kakadiaris et al. | |
| 2010/0278410 A1 | 11/2010 | Ohishi | |
| 2011/0044524 A1* | 2/2011 | Wang et al. | 382/131 |
| 2011/0145053 A1* | 6/2011 | Hashim-Waris | 705/14.35 |

OTHER PUBLICATIONS

"Analysis of Spatio-Temporal Prediction Methods in 4D Volumetric Medical Image Datasets," Uwe-Erik Martin et al, ICME 2008, pp. 525-528, 2008.*

"Efficient Lossless Compression of 4-D Medical Images Based on the Advanced Video Coding Scheme," Victor Sanchez et al, IEEE Transactions on Information Technology in Biomedicine, vol. 12, No. 4, Jul. 2008, pp. 442-446.*

Zagar, M. et al., "Lossless and Lossy Compression in 4D Bio-modeling," CTA '07, Apr. 12-14, Hammamet, Tunisia.

Strickland, N. H., "Multidetector CT: what do we do with all the images generated?" The British Journal of Radiology, 77, S14-19, Dec. 2004.

* cited by examiner

METHOD AND SYSTEM FOR TRANSFER OF CARDIAC MEDICAL IMAGE DATA FILES

CROSS-REFERENCE TO RELATED APPLICATIONS

The present application is a non-provisional filing claiming priority to U.S. Provisional Patent Application Ser. No. 61/150,173, which was filed in the U.S. Patent Office on Feb. 5, 2009, and which is expressly incorporated herein in its entirety by reference thereto.

FIELD OF INVENTION

The present invention relates generally to the fast transfer of image data files. The present invention relates more specifically to a system and method for the fast transfer of medical image data files.

BACKGROUND

Various symptoms experienced by individuals can be in-part diagnosed using an imaging device. Acute chest pain is presently a major health issue, constituting several million emergency department (ED) visits annually in the United States. The present standard of care for diagnosing such, e.g., chest pain, involves using serial blood tests and stress tests. Such tests, often administered in serial, are time consuming, costly, and sometimes inaccurate.

While a multi-detector computed tomography device is believed to be one of the most accurate non-invasive diagnostic imaging tests available for ruling out the presence of coronary artery disease, among other things, only a very small number of practicing physicians and technicians are qualified to operate and interpret CT angiography (CTA). Further, currently available MDCT devices do not have sufficient speed to sufficient catch the unmoving image of a beating heart or other object during scanning. Accordingly, less clear images result which are not easily transmittable to a remote location for review given the lack of clarity. For example, a typical chest CT study only includes about sixty images. If the patient's heart rate is not slower than 65 beats/minute during the scan, the number of images taken may increase to 3000 or more to account for such. And, downloading, transmission, manipulation, and/or processing of such a large volume of data is extremely costly and time consuming. Further, since many emergency departments and other locations lack a resident expert of the CT device or other imaging devices, remote access and overview would be helpful, except that such data volume would be difficult to transmit in such a situation. Accordingly, the present invention described herein provides systems and methods for timely and cost efficient use of CT and other imaging devices by hospitals and other service providers.

SUMMARY

Embodiments of the present invention provide for a system and method in which transfer of an image data file, e.g., a medical image data file, is effected in an expedient and efficient manner.

Embodiments of the present invention provide for a system and method for the transfer of an image data file, including: acquiring device scan slices of an object per time point, selecting a portion of the device scan slices of the object per time point which illustrate a change in the object from a previous time point, forming at least one optical temporal image in spiral fashion per time interval from the selected portion, and transmitting the at least one optical temporal image as an image data file to a location. Embodiments of the present invention provide for a system and method in which the forming of the optical temporal image includes compressing the device scan slices.

Embodiments of the present invention provide for a system and method in which at least one of a 3-dimensional and differential 2-dimensional lossless compression technique is used. Embodiments of the present invention provide for a system and method in which the forming of the optical temporal image includes transcoding the device scan slices, e.g., from motion-JPEG to H.264.

Embodiments of the present invention provide for a system and method in which the device is a computed tomography machine or multi-detector computed tomography machine. Embodiments of the present invention provide for a system and method in which the object being imaged is at least one of a body organ, a heart, a lung, a liver, a gall bladder, an eye, an artery, and a brain.

Embodiments of the present invention provide for a system and method in which the portion is made of one scan slice from every ten scan slices acquired in succession. Embodiments of the present invention provide for a system and method including extracting a specific area of interest from each of the at least one optical temporal images for transmission as the image data file.

Embodiments of the present invention provide for a system and method in which the transmission occurs via at least one of a wired network and a wireless network.

Embodiments of the present invention provide for a system and method which includes evaluating the transmitted image data file by the location, determining full diagnostics from the transmitted medical imaging data, and transmitting the full diagnostics to at least one of a storage location and a use location.

Embodiments of the present invention provide for a system and method in which the storage location is at least one of a server, a plurality of servers, a storage device, a magnetic strip storage device, a chip storage device. In embodiments of the present invention, the use location is at least one of a hospital, a location from where the image data file was acquired, a university, a clinic, and another evaluation location to check accuracy of the full diagnostics.

In embodiments of the present invention, the evaluation of the transmitted image data is effected by at least one of an urgent care clinic, a large cardiology practice group, a primary care practice group, a hospital, a university, and a location remote from where the image data was acquired.

In embodiments of the present invention, the image data file is compressed further for faster transfer of data via at least one of the Internet and a video conference system, and/or via download to a storage device.

Embodiments of the present invention provide for a system and method for the transfer of an image data file, including: acquiring device scan slices of an object per time point, selecting a best image from one or more subsets of the device scan slices of the object per time point, forming at least one optical temporal image in spiral fashion per time interval from the best images, and transmitting the at least one optical temporal image as an image data file to a location. In an embodiment, for example, a certain number, e.g., ten, of time points are found to cover the entire cardiac cycle. That certain number of time points can be viewed as a subset. The "best," e.g., a relatively clear scan, a motion-free scan, is then selected from the subset. For example, if the scan is of a heart, a "best" image may be one which shows each of the main arteries clearly. Each of these "best" images is then used to form the at least one optical temporal image in spiral fashion per time interval, which can then be transmitted to a location, e.g., an outside clinic or storage server.

Embodiments of the present invention provide for a system and method for the transfer of an image data file, including: acquiring device scan slices of an object per time point, forming at least one optical temporal image in spiral fashion per time interval from the device scan slides, extracting a specific area of interest from each of the at least one optical temporal images, and transmitting the extracted parts of the at least one optical temporal images as an image data file to a location. Alternatively, the extraction is done to the device scan slices, and then an optical temporal image is formed from the extracted part of the device scan slices.

Embodiments of the present invention provide for a method and system for the remote evaluation of medical imaging data, including: an imaging device, the imaging device generating imaging device scan slices of an object per time point, a processor, the processor being configured to select a portion of the imaging device scan slices which illustrate change in the object from a previous time point, and a compression device, the compression device forming at least one optical temporal image in spiral fashion per time interval from the selected portion. In embodiments of the present invention, the at least one optical temporal image is transmitted as an image data file having sufficient resolution required for its intended review use. In embodiments of the present invention, the image data file is transmitted to a remote location for at least one of storage and review. In embodiments of the present invention, the imaging device includes at least one multi-detector computed tomography scan.

In embodiments of the present invention, the compression device includes a transcoder for transcoding the imaging device scan slices from motion-JPEG to H.264. In embodiments of the present invention, the portion is made of one scan slice from every ten scan slices acquired in succession. In embodiments of the present invention, at least one of the processor and a separate processor extracts a specific area of interest from each of the at least one optical temporal images for transmission as the image data file.

DETAILED DESCRIPTION

Figure 1:
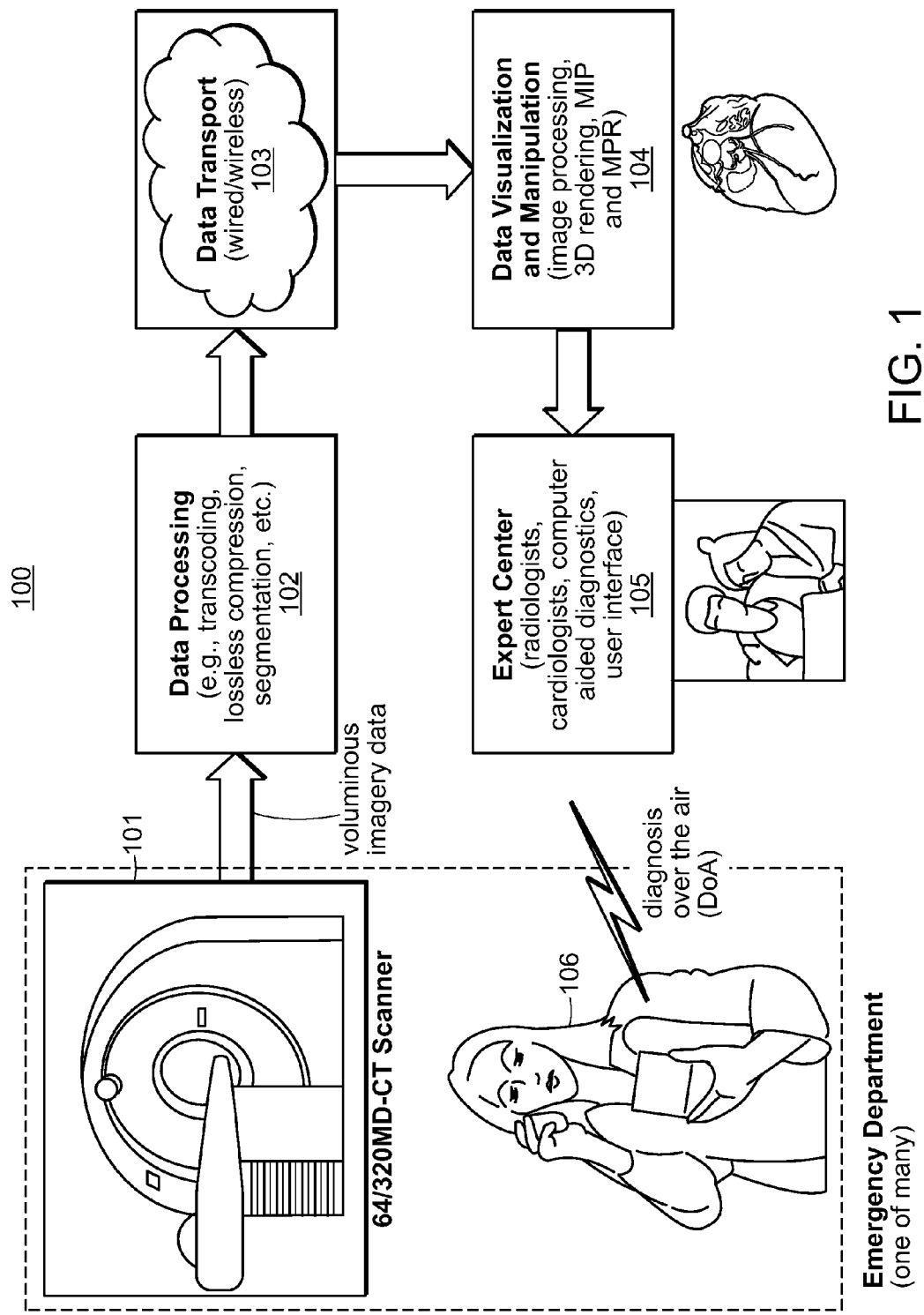
FIG. 1 is a flowchart showing a remote evaluation system and method according to an example embodiment of the present invention.

FIG. 1 is a flowchart showing a remote evaluation system and method according to an example embodiment of the present invention. For example, such a remote evaluation system 100 can involve a medical scanning device 101 such as, e.g., a multi-detector computed tomography device (MDCT) or other imaging device. Such imaging devices 101 can provide voluminous amounts of imagery data. Such volume can be in memory size and/or number of scans or scan slices. The imagery data is then processed 102 using, e.g., transcoded, lossless compression technique, segmentation, each of which data processing applications can be running on a computer, processor, or other machine, as discussed herein, and then sent to another location. For example, such sending or transmission can be via a wired connection or wireless connection 103 to another machine, another location, or to a data storage location such as a chip card. Alternatively, such sending or transmission can be via a video conferencing capability in which the images can be viewed as they are being transmitted. The processed images may then be further processed 104. For example, such processing can be to convert the files to a viewable state by the remote location. For example, such processing can be to render a 2-dimensional or 3-dimensional image from the data. Other medical imaging devices (MIP) and/or multiplanar reconstruction devices (MPR), may be used. Once any desired data visualization and/or manipulation 104 takes place, the processed data is sent to, e.g., an expert center 105. At an expert center, for example, an expert, other qualified individual and/or processing application reviews the processed data to determine a diagnosis. In such a system, the expert center representative or processor may contact the originating source 106, e.g., a hospital emergency department, for the data with the diagnosis. For example, the processor may send a text message, email, electronic voicemail, and/or page to the intended destination to advise of the diagnosis.

Figure 2:
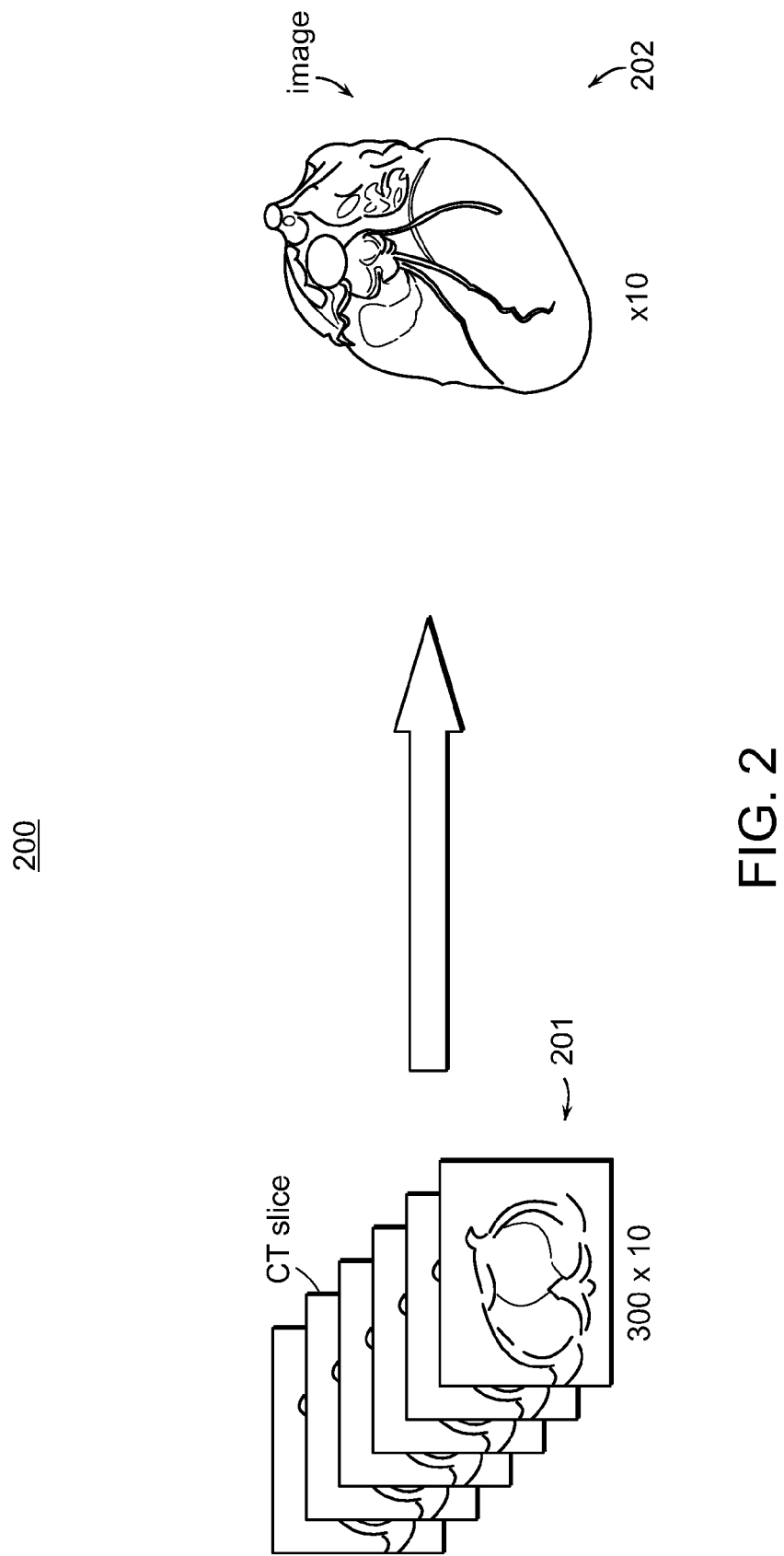
FIG. 2 is a diagram showing an example of spatial compensation according to an embodiment of the present invention.

FIG. 2 is a diagram showing an example of spatial compensation 200 according to an embodiment of the present invention. In FIG. 2, a spatial compensation of the image is shown. That is, for example, assume that about three hundred computed tomography (CT) scan slices construct one entire heart image per time point. Instead of transmitting the entire three hundred slices, which uses memory and takes transmission time, one can leverage existing video compression techniques in order to reduce the number of image slices needed. For example, the image device may produce CT scan slices 201 as motion-Joint Photographic Experts Group (MJPEG or M-JPEG) image files. Certain available video compression techniques, e.g., the International Telecommunication Union-Telecommunication Standardization Sector (ITU-T) H.264 standard or other block-oriented motion-compensation-based codec standard, may be used to pull every nth scan slice which is a full JPEG file. Such files can then be assembled for use and transmission, thus, eliminating significant memory waste and transmission time. The other files in the set are included for spatial compensation, and not needed unless, for example, if the file shows any difference in the object from the previous time point scan slice(s). In this manner, in one estimation, one may eliminate possibly 10% or more in image byte size.

Figure 3:
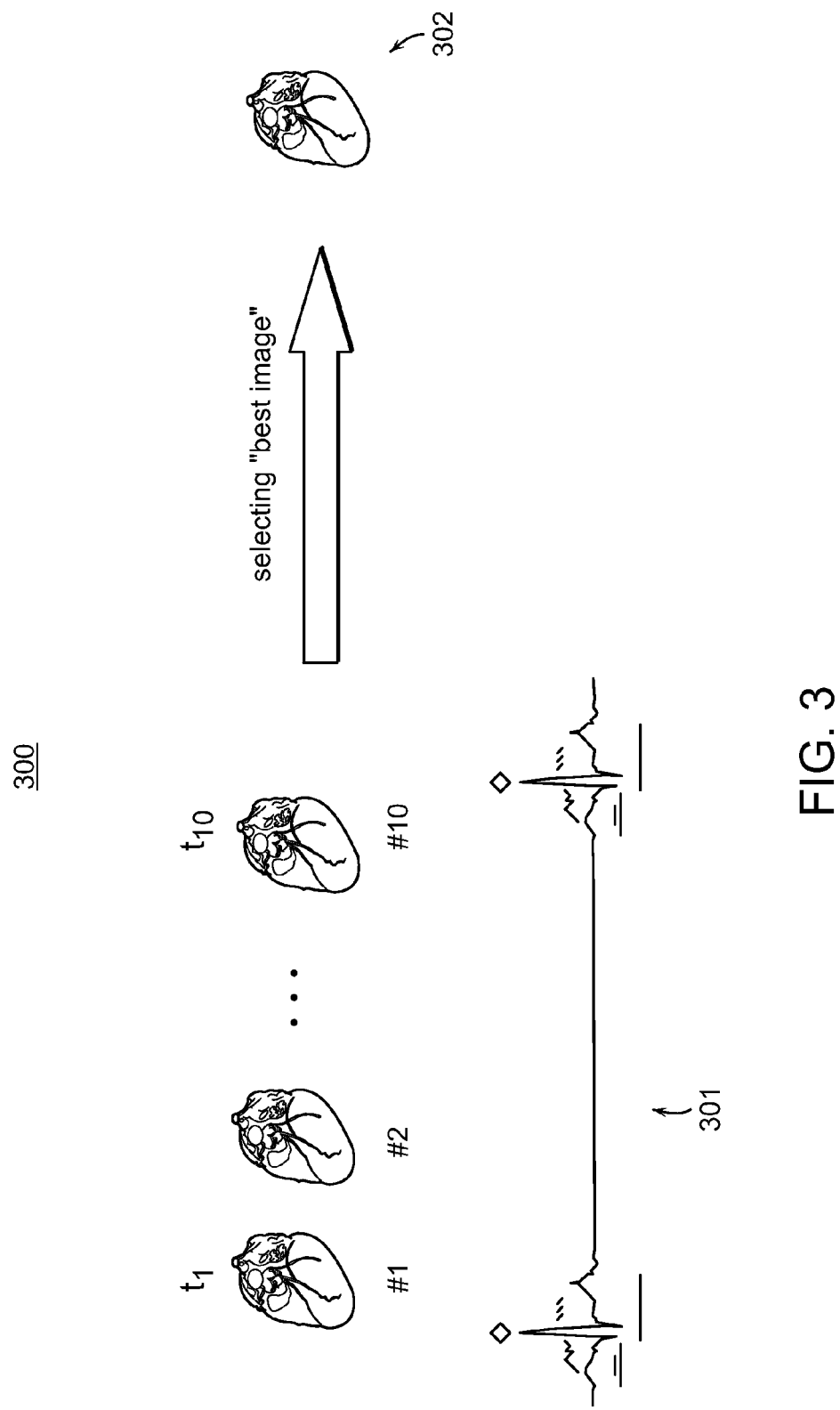
FIG. 3 is a diagram showing an example of optimized selection according to an embodiment of the present invention.

FIG. 3 is a diagram showing an example of optimized selection 300 according to an embodiment of the present invention. One can observe the number of time points which cover an entire cycle of an organ. For example, one observes that about ten time points cover an entire cardiac cycle. Then, the "best" image(s) are selected from the ten time points. This selection may be done manually and/or by a processor. For example, of heart scan slices 301 from one to ten, one image is thus selected as a clear image, e.g., when the organ such as a heart was relatively motion-free and all major coronary arteries are clearly viewable.

Figure 4:
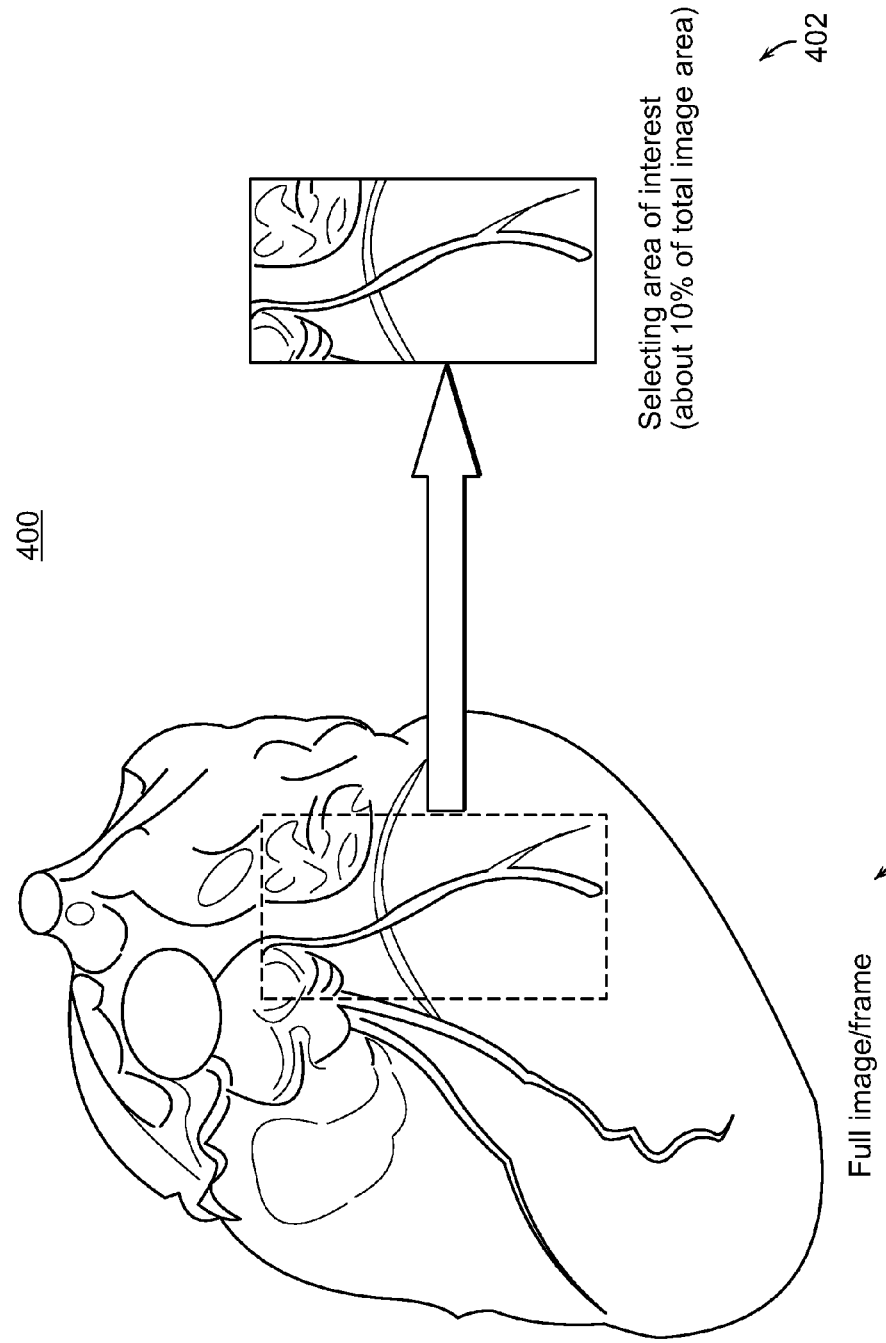
FIG. 4 is a diagram showing an example segmentation according to an embodiment of the present invention.

FIG. 4 is a diagram showing an example segmentation 400 according to an embodiment of the present invention. For example, if one is interested only in a specific region of an object 401, such as a heart in this example, then just the cut of that region 402 is selected and further images and processed. Such selection can be sometimes only a small fraction of the entire image, thus providing significant reduction in memory and transmission time.

It is also noted, that processing of images in the embodiments can cost significant time and money—which is alleviated in part by the various embodiments of the present invention.

In an embodiment, for example, if one assumes that 3000 scan slices per patient is acquired, each scan slice having a size of about 500 kilabytes. Then, the total data file size per patient is calculated to be 3000×500 kilabytes=1.5 gigabytes of memory. After the above-described embodiments are implemented, such memory can be reduced significantly. For example, it may be estimated in some instances, that the memory is reduced by a factor of 100 or even 1000, which is suitable for moderate speed wireless transmissions or other transmissions. Accordingly, such files can then be timely transmitted to a remote center for diagnosis of appropriate resolution sized files. Such efforts can assist emergency and other departments in faster, more accurate, and less costly, diagnosis.

It should be understood that there exist implementations of other variations and modifications of the invention and its various aspects, as may be readily apparent to those of ordinary skill in the art, and that the invention is not limited by specific embodiments described herein. Features and embodiments described above are combinable with and without each other. It is therefore contemplated that the present invention covers any and all modifications, variations, combinations or equivalents that fall within the scope of the basic underlying principals disclosed and claimed herein.

What is claimed is:

1. A computer implemented method for remote diagnosis of coronary artery disease, the method comprising:
    imaging a heart of a patient of a hospital emergency department using a scanning multi-detector computed tomography device at an imaging location, the computed tomography device generating heart image data including three dimensional cardiac image data of a plurality of coronary arteries of the patient;
    storing the image data in a server;
    processing the image data with a computer to select a subset of the image data for transmission to a remote location, said processing including:
    selecting motion free cardiac image data;
    subsequently segmenting the motion free image data to select coronary artery image data from the stored image data to extract the selected coronary artery image data from the heart image data;
    compressing the coronary artery extracted image data including lossless compression of the selected coronary artery image data to generate compressed coronary artery image data;
    transmitting the compressed coronary artery image data to a remote location;
    recording a remote diagnosis of the coronary arteries of the patient to store data indicating coronary artery disease of the patient;
    storing the transmitted compressed coronary artery image data; and
    wirelessly transmitting the remote diagnosis to a display device.

2. The method of claim 1, further comprising compressing the device scan slices from three dimensional data to at least one two-dimensional image.

3. The method of claim 1, wherein the method comprises transcoding the image data from motion-JPEG to H.264.

4. The method of claim 1, further comprising transmitting image data by video conference from the image data generated by the computed tomography device.

5. The method of claim 1, wherein the compressed image data is transmitted to a hand-held wireless device.

6. The method of claim 1, wherein the compressed image data comprises one scan slice from every ten scan slices acquired in succession.

7. The method of claim 1, further comprising:
    extracting a specific coronary artery of interest from at least one motion free image for transmission as the image data file.

8. The method of claim 1, wherein the wireless transmission occurs via at least one of a wired network and a wireless network to an emergency department display.

9. The method of claim 1, further comprising:
    imaging the heart at a heart rate of at least 65 beats per minute;
    evaluating the transmitted image data file at the imaging location;
    recording a diagnostic evaluation from the transmitted imaging data; and
    transmitting the evaluation to at least one of a storage location and a use location.

10. The method of claim 9, wherein the storage location is at least one of a server, a plurality of servers, a storage device, a magnetic strip storage device, a chip storage device.

11. The method of claim 9, wherein an evaluation of the transmitted image data is effected by at least one of an urgent care clinic, a large cardiology practice group, a primary care practice group, a hospital, a university, and a location remote from where the image data was acquired.

12. The method of claim 9, wherein the image data file is compressed further for faster transfer of data via at least one of the Internet and a video conference system.

13. A computed tomography system for the remote evaluation of cardiac medical imaging data, comprising:
    a computed tomography (CT) imaging device for imaging a patient of a hospital emergency department, the CT imaging device generating cardiac image data of a heart of the patient;
    a processor connected to the CT imaging device, the processor being configured to select a portion of the cardiac image data which illustrate change in the heart from a previous time, the processor being operative to compress the cardiac image data by forming a compressed image data file from the selected portion of the cardiac image data and segmenting the compressed cardiac image data to extract at least one coronary artery image data file from the cardiac image data; and
    a wireless network connected to the processor wherein at least one coronary artery image data file is transmitted to a remote location for diagnosis of coronary artery disease wherein a diagnosis is transmitted by wireless transmission to an emergency department display device.

14. The system of claim 13, wherein the extracted coronary artery image data file is transmitted to the remote location for at least one of storage and review.

15. The system of claim 13, wherein the CT imaging device includes at least one multi-detector scanning computed tomography imaging system connected to a server, the CT imaging device operable to generate 3000 or more cardiac images during a scan.

16. The system of claim 13, wherein the compression device includes a transcoder for transcoding the stored image data from motion-JPEG to H.264.

17. The system of claim 13, wherein the compressed image data is generated from every ten scan slices acquired in succession.

18. The system of claim 13, wherein at least one of the processor and a separate processor extracts a specific area of interest from each of the at least one coronary artery image data file for transmission as the image data file.

19. A method of imaging a heart of a patient to diagnose coronary artery disease, the method comprising:
   imaging a heart of a patient with a scanning multi-detector computed tomography device connected to a hospital server;
   generating an image data file of the heart that includes three dimensional coronary artery image data of the heart;
   processing the image data file to reduce file size and thereby generate a reduced data image file that includes a-segmented image data of at least one coronary artery that has been extracted from the image data file of the heart;
   sending the reduced data image file including the extracted image data of the at least one coronary artery to a remote location with the hospital server;
   electronically storing a coronary artery disease diagnosis associated with the reduced data image file of the at least one coronary artery; and
   transmitting the stored diagnosis and the reduced data image file of the at least one coronary artery by wireless communication to a wireless display device.

20. The method of claim 19 further comprising processing image data with a multiplanar reconstruction device.

21. The method of claim 19 further comprising transcoding the reduced data image file for wireless transmission.

22. The method of claim 19 further comprising conducting a video conference for remote viewing of the image data file.

23. The method of claim 19 wherein the step of processing the image data file comprises segmenting the image data file to generate a plurality of coronary artery image files for a corresponding plurality of coronary arteries of the patient.

24. The method of claim 19 further comprising sending the three dimensional coronary artery image data to a remote diagnosis location with the hospital server.

25. The method of claim 19 further comprising sending the diagnosis by e-mail transmission.

26. The method of claim 19 further comprising imaging a heart having a heart rate of at least 65 beats per minute.

27. The method of claim 19 further comprising taking 3000 or more images during a computed tomography scan.

* * * * *